(12) United States Patent
Akira et al.

(10) Patent No.: US 7,608,750 B2
(45) Date of Patent: Oct. 27, 2009

(54) NONHUMAN MODEL ANIMAL UNRESPONSIVE TO IMMUNOPOTENTIATING SYNTHETIC COMPOUND

(75) Inventors: Shizuo Akira, Osaka (JP); Hideyuki Tomizawa, Saitama (JP); Takashi Yamaoka, Hyogo (JP)

(73) Assignees: Japan Science and Technology Agency, Kawaguchi-shi (JP); Dainippon Sumitomo Pharma Co., Ltd., Osaka-shi (JP)

( * ) Notice: Subject to any disclaimer, the term of this patent is extended or adjusted under 35 U.S.C. 154(b) by 243 days.

(21) Appl. No.: 10/496,501

(22) PCT Filed: Nov. 22, 2002

(86) PCT No.: PCT/JP02/12234

§ 371 (c)(1),
(2), (4) Date: Jul. 28, 2004

(87) PCT Pub. No.: WO03/043588

PCT Pub. Date: May 30, 2003

(65) Prior Publication Data

US 2005/0235372 A1    Oct. 20, 2005

(30) Foreign Application Priority Data

Nov. 22, 2001    (JP)    ............... 2001-358295

(51) Int. Cl.
*A01K 67/00* (2006.01)
*A01K 67/027* (2006.01)
*C12N 15/00* (2006.01)

(52) U.S. Cl. .............................. 800/25; 800/13; 800/14; 800/18

(58) Field of Classification Search .................... 800/13, 800/14, 18, 25
See application file for complete search history.

(56) References Cited

U.S. PATENT DOCUMENTS 6,943,240 B2 *    9/2005    Bauer et al. ................ 536/23.1

FOREIGN PATENT DOCUMENTS

WO    WO 03/043572 A2    5/2003

OTHER PUBLICATIONS

Capecchi, Mario R., 1989, TIG, vol. 5, No. 3, p. 70-76.*
Leonard et al., 1995, Immunological Reviews, vol. 148, pp. 97-114.*
Rescher et al., 2004, Journal of Cell Science, vol. 117, p. 2631-2639.*
Mogil et al., 1999, Pain, vol. 80, pp. 67-82.*
Sigmund, C., Jun. 2000, Arterioscler. Thromb. Vasc. Biol., p. 1425-1429.*
Tsung-Hsien Chuang et al., "Cloning and characterization of a subfamily of human Toll-like receptors: hTLR7, hTLR8 and hTLR9", Eur. Cytokine Netw., Sep. 2000, pp. 372-378, vol. 11, No. 3.
Xin Du et al., "Three novel mammalian toll-like receptors: gene structure, expression, and evolution", Eur. Cytokine Netw., Sep. 2000, pp. 362-371, vol. 11, No. 3.
Osamu Takeuchi et al., "Cutting Edge: Preferentially the T-Stereoisomer of the Mycoplasmal Lipopeptide Macrophage-Activating Lippopeptide-2 Activates Immune Cells Through a Toll-Like Receptor 2- and MyD88-Dependent Signaling Pathway", The Journal of Immunology, Jan. 2000, pp. 554-557.
Gail A. Bishop et al., Molecular Mechanisms of B Lymphocyte Activation by the Immune Response Modifier R-848, The Journal of Immunology, 2000, pp. 5552-5557, vol. 165.
Hiroaki Hemmi et al., "Small Anti-Viral Compounds Activate Immune Cells Via the TLR7 My D88-Dependent Signaling Pathway", Nature Immunology, vol. 3, No. 2, Feb. 2002, pp. 196-200.
Marion Jurk et al., "Human TLR7 or TLR8 Independently Confer Responsiveness to the Antiviral Compound R-848", Nature Immunology, vol. 3, No. 6, Jun. 2002, p. 499.
Galli-Taliadoros, L.A., et al., (1995) Gene knock-out technology: a methodological overview for the interested novice, Journal of Immunological Methods, vol. 181, pp. 1-15.

* cited by examiner

*Primary Examiner*—Shin-Lin Chen
(74) *Attorney, Agent, or Firm*—Foley & Lardner LLP

(57) ABSTRACT

The present invention relates to provide a non-human animal model unresponsive to a synthetic compound wherein a gene function encoding TLR7 that recognizes an immunopotentiating synthetic compound such as imidazoquinoline lacks on is genomic locus. Whole or part of a gene fragment of a gene site including an intracellular region and a transmembrane region of a TLR7 gene obtained from a mouse gene library is replaced by a plasmid including poly A signal and a marker gene to construct a targeting vector. Then, this targeting vector is linearized and transferred into embryonic stem cells. The target embryonic stem cells wherein the TLR7 gene function is deleted are microinjected into a mouse blastocyst to generate a chimeric mouse. Then, this chimeric mouse is crossed with a wild-type mouse to generate a heterozygote mouse. Next, the heterozygote mice are intercrossed to obtain a TLR7 knockout mouse.

7 Claims, 11 Drawing Sheets

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide (phosphorothioate 1668)

<400> SEQUENCE: 1

-continued

```
tccatgacgt tcctgatgct                                         20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide D19

<400> SEQUENCE: 2
ggtgcatcga tgcagggggg                                         20

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide AAC-30

<400> SEQUENCE: 3
accgataacg ttgccggtga cggcaccacg                              30

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide (phosphodiester 1668)

<400> SEQUENCE: 4
ttcatgacgt tcctgatgct                                         20

<210> SEQ ID NO 5
<211> LENGTH: 430
<212> TYPE: DNA
<213> ORGANISM: Homo sapiens

<400> SEQUENCE: 5
gtaaaagagt ggcaagtaaa aaacatgggg ctctgattct cctgtaattg tgataattaa    60
atatacacac aatcatgaca ttgagaagaa ctgcatttct acccttaaaa agtactggta   120
tatacagaaa tagggttaaa aaaaactcaa gctctctcta tatgagacca aaatgtacta   180
gagttagttt agtgaaataa aaaaccagtc agctggccgg gcatggtggc tcatgcttgt   240
aatcccagca ctttgggagg ccgaggcagg tggatcacga ggtcaggagt ttgagaccag   300
tctggccaac atggtgaaac cccgtctgta ctaaaaatac aaaaattagc tgggcgtggt   360
ggtgggtgcc tgtaatccca gctacttggg aggctgaggc aggagaatcg cttgaacccg   420
ggaggtggag                                                         430
```

NONHUMAN MODEL ANIMAL UNRESPONSIVE TO IMMUNOPOTENTIATING SYNTHETIC COMPOUND

TECHNICAL FIELD

The present invention relates to a non-human animal model unresponsive to synthetic compounds such as imidazoquinoline group compound R-848 and the like, wherein a gene function encoding TLR7 that recognizes synthetic compounds specifically such as imidazoquinoline group compound R-848 and the like lacks on its genomic locus, a screening method for substances for inhibiting or promoting a response to synthetic compounds such as imidazoquinoline group compound R-848 by using these non-human animal model, and a screening method for an immunopotentiating synthetic compound and the like.

BACKGROUND ART

A Toll gene is known to be necessary for patterning dorsoventral axis while an embryo is developing in Drosophila (Cell 52, 269-279, 1998; Annu. Rev. Cell Dev. Biol. 12, 393-416, 1996), and for an antifungal immune response in an adult body (Cell 86, 973-983, 1996). The Toll is a type-I transmembrane receptor with an extracellular domain including leucine-rich repeats (LRRs) and this intracellular domain has been elucidated that it demonstrates high homology with that of mammalian interleukin-1 receptor (IL-1R) (Nature 351, 355-356, 1991; Annu. Rev. Cell Dev. Biol. 12, 393-416, 1996; J. Leukoc. Biol. 63, 650-657, 1998).

Recently, mammalian homologs of Toll, called Toll-like receptors (TLR) were identified, and heretofore, 10 families such as TLR2, TLR3, TLR4, TLR6, TLR7, TLR8, TLR9, and TLR10 have been reported (Nature 388, 394-397, 1997; Proc. Natl. Acad. Sci. USA 95, 588-593, 1998; Blood 91, 4020-4027, 1998; Gene 231, 59-65, 1999). This TLR family is known that it recruits IL-1R-associated kinase (IRAK) through MyD88 which is an adapter protein as well as aforementioned IL-1R, and then activates downstream mitogen-activated protein (MAP) kinase and NF-κB which is a nuclear factor (J. Exp. Med. 187, 2097-2101, 1998; Mol. Cell 2, 253-258, 1998; Immunity 11, 115-122, 1999). In addition, it is also believed that the role of TLR family in mammals is related to innate immune recognition as a pattern recognition receptor (PRR) that recognizes the consensus structure of bacteria (Cell 91, 295-298, 1997).

One of pathogen-associated molecular patterns (PAMPs) recognized by the aforementioned PRR is a lipopolysaccharide (LPS) which is a principal component of outer-membrane of Gram-negative bacteria (Cell 91, 295-298, 1997). It is known that host cells are stimulated by the LPS to generate various kinds of inflammatory cytokines such as TNF-α, IL-1 and IL-6 and the like on the host cells (Adv. Immunol. 28, 293-450, 1979, Annu. Rev. Immunol. 13, 437-457, 1995), and LPS captured by LPS-binding protein (LBP) is delivered to CD14 on cell surface (Science 249, 1431-1433, 1990; Annu Rev. Immunol. 13, 437-457, 1995). The present inventors generated knockout mice of TLR4 and reported that TLR4 knockout mice are unresponsive to LPS which is a principal component of the aforementioned outer-membrane of Gram-negative bacteria (J. Immunol. 162, 3749-3752, 1999). They generated TLR2 knockout mice and reported that macrophages of themselves lower the reactivity to Gram-positive bacteria cell walls or peptidoglycan which is a component thereof (Immunity, 11, 443-451, 1999), and that biological reaction is induced via TLR2 and MyD88 signaling pathway (J. Immunol. 164, 554-557, 2000).

Further, the present inventors compared/analyzed TLR6 knockout mice, wild-type mice and TLR2 knockout mice to clarify that TLR6 is a receptor protein specifically recognizing mycoplasma-derived lipoproteln/lipopeptide. They also found full length cDNA (GenBank Accession No. AF245704) for TLR9 and clarified that TLR9 is a receptor protein specifically recognizing bacterial DNA including unmetylated CpG sequence. Moreover, two new members of TLR7 and TLR8 are registered to GenBank (Accession No. AF240467 and AF246971).

On the other hand, imiquimod, which is an immune response-modulator that have been found when screening antiherpesvirus activity, shows antivirus activity and antitumor activity in animal model. It is clarified this agent shows antivirus activity and antiproliferative activity by inducing cytokines such as IFN-α, IL-6 and IL-12, similarly to a secondary induction of IFN-γ in various types of cells (J. Leukoc. Biol. 58, 365-372, 1995; J. Interferon Res, 1989; S2115, Antimicrob. Agents Chemother. 38, 2059-2064, 1994; Am. J. Clin. Pathol. 102, 768-774, 1994), and that imiquimod stimulates NF-κB and MAP kinase (J. Immunol. 165, 5552-5557, 2000; Mol. Cell. Biol. 15, 2207-2218, 1995), as well. In addition, imiquimod and its related compounds are known to inhibit the replication of type 2 herpes simplex virus and cytomegalovirus (J. Infect. Dis. 183, 844-849, 2001; Antimicrob. Agents Chemother. 32, 678-83, 1988). In actual treatment, it is reported that imiquimod is effective for treating pudendal wart (*condyloma acuminatum*) caused by human papilloma virus (Sex. Transm. Infec. 76, 162-8, 2000), and that resiquimod which is a derivative of imiquimod, abbreviated as R-848, is also effective for treating genital herpes (JAMA 285, 2182-2183, 2001). The structural formulae of these imiquimod and R-848 that are imidazoquinoline group compounds are shown as follows:

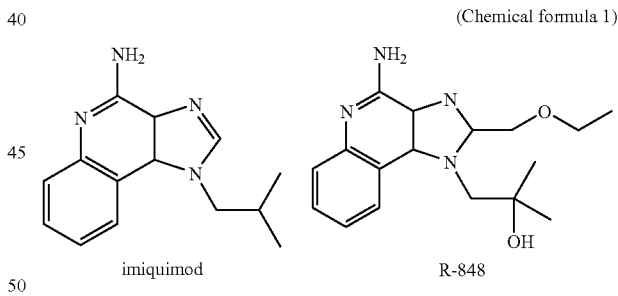

(Chemical formula 1)

TLR families are known to be receptors, involved in recognizing the components of pathogens, and it has been clarified by the present inventors that the components derived from various kinds of bacteria and mycoses are recognized by TLR family, as mentioned above. In other words, the present inventors have already generated TLR2-, TLR4-, TLR6-, and TLR9-deficient mice, and revealed that TLR4, TLR2, TLR6, and TLR9 are receptors which respond to lipopolysaccharide (LPS), to pepridoglycan and lipopeptide derived from Gram-positive bacteria, to polypeptide of mycoplasma similarly to TLR2, and to bacterium DNA including non-methylate CpG sequence, respectively. However, it is still unknown which substances the other TLR family member such as TLR3, TLR7, TLR8 or TLR10 and the like recognizes. In addition, proteins, which can recognize immunopotentiating synthetic compounds, have been unknown.

The object of the present invention is to provide a relationship between each member of TLR family to signaling by stimulation with an immunopotentiating synthetic compound in vivo, particularly a non-human animal model unresponsive to synthetic compounds, wherein a gene function that encodes TLR7 recognizing immunopotentiating synthetic compounds lacks on its genomic locus, said compound being useful to elucidate the relationship of each TLR family member toward signaling by stimulation of immunopotentiating synthetic compounds in vivo, particularly the role of TLR7 in vivo, particularly a non-human animal wherein the gene function of TLR7 lacks on its genomic locus, a screening method for substances for inhibiting or a promoting a response to an immunopotentiating synthetic compound by using the above-mentioned non-human animal models, and a screening method for an immunopotentiating synthetic compound.

The present inventors generated MyD88-deficient mice, and already reported that the macrophages derived from MyD88-deficient mice do not respond to any of TLR ligands when producing cytokines. Since it is not possible to confirm the response in cells of MyD88-deficient mice, various kinds of compounds which might activate cells via TLR were examined. Large number of compounds were screened, and through the process of inducing cytokines from mononuclear leukocytes or macrophages, imidazoquinoline group compounds which might induce humoral immunity and cellular immunity, i.e. imidazoquinoline group compounds such as imiquimod, R-848 and the like which act on various cells and which are known as an immunopotentiator inducing generation of inflammatory cytokines such as IFN-α, IL-6 and IL-12 and the like were treated as target compounds. Meanwhile, the primary structure of the protein of TLR7 is quite similar to that of TLR9 which recognizes microbial DNA. However, the lack of reactivity to microbial DNA is not observed in TLR7-deficient mice as in TLR9-deficient mice. Then, TLR7-deficient mice of TLR family were generated, and the substances recognized by TLR7 were screened subsequently having a TLR7 as a target.

Then, the present inventors stimulated TLR7-deficient mice with R-848 and found that induction of generation of inflammatory cytokines from macrophages, induction of proliferation of B cells, and induction of maturation of dendritic cells were not observed at all. Moreover, in macrophages derived from TLR7-deficient mice, the activation of intracellular signals such as NF-κB, JNK, IRAK by stimulation with R-848 was not observed at all. This suggests that TLR7 is involved not only in recognition of components of pathogen but also of a synthetic compound. Considering that the reactivity to R-848 was completely defective also in MyD88-deficient mice, wherein MyD88 is an adapter molecule that plays an essential role to TLR family signaling pathway, it was thought that TLR7 was an essential receptor for recognition of imidazoquinoline group compounds R-848, and imidazoquinoline group compounds R-848 exerted adjuvanticity by signaling pathway via TLR7-MyD88. As imidazoquinoline group compounds R-848 has an intensive antiviral action and immunopotentiating effect for immune cells, and used for treating actually human pudendal wart caused by papilloma virus, it was thought that TLR7-deficient mice could be not only a very useful model mice for elucidating the action mechanism of imidazoquinoline group compounds, but also to be a very useful model mice for clinical application of synthetic compound agents such as a therapeutic agent for viral infectious diseases, with TLR7 as a target. The present invention has been completed based on the above-mentioned knowledge.

DISCLOSURE OF THE INVENTION

The present invention relates to a non-human animal model unresponsive to an immunopotentiating synthetic compound, wherein a gene function that encodes TLR7 recognizing an immunopotentiating synthetic compound is deficient on its genomic locus ("1"); the non-human animal model unresponsive to an immunopotentiating synthetic compound according to "1", wherein the non-human animal is a rodent ("2"); the non-human animal model unresponsive to an immunopotentiating synthetic compound according to "2", wherein the rodent is a mouse ("3"); the non-human animal model unresponsive to an immunopotentiating synthetic compound according to "3", wherein the mouse is a TLR7 knockout mouse obtained by constructing a targeting vector by replacing whole or a part of a gene fragment of a gene site including an intracellular region and a transmembrane region of a TLR7 gene obtained by screening from a mouse gene library using a probe derived from a mouse EST clone with a plasmid including a poly A signal and a marker gene, by introducing the linearized targeting vector into embryonic stem cells, by microinjecting the targeted embryonic stem cell whose TLR7 gene function is deficient into a blastcyst of the mouse to generate a chimeric mouse, by intercrossing the chimeric mouse with a wild-type mouse to generate a heterozygote mouse, and by intercrossing the heterozygote mice ("4"); the non-human animal model unresponsive to an immunopotentiating synthetic compound according to any one of "1" to "4", wherein the immunopotentiating synthetic compound is an imidazoquinoline group compound ("5"), and the non-human animal model unresponsive to an immunopotentiating synthetic compound according to "5", wherein the imidazoquinoline group compound is R-848 ("6").

The present invention also relates to a screening method for a substance for inhibiting or promoting a response to an immunopotentiating synthetic compound, wherein the response to the immunopotentiating synthetic compound in immune cells derived from the non-human animal model unresponsive to an immunopotentiating synthetic compound according to any one of "1" to "6" is measured/evaluated with the use of the aforementioned immune cells, a test substance and the immunopotentiating synthetic compound ("7"); a screening method for a substance for inhibiting or promoting a response to an immunopotentiating synthetic compound, wherein the response to the immunopotentiating synthetic compound of the non-human animal model unresponsive to an immunopotentiating synthetic compound according to any one of "1" to "6" is measured/evaluated with the use of aforementioned non-human animal model, a test substance and the immunopotentiating synthetic compound ("8"); a screening method for a substance for inhibiting or promoting a response to an immunopotentiating synthetic compound according to "7" or "8", wherein the comparison/evaluation with a wild-type non-human animal as a control is performed in measurement/evaluation of the response to an immunopotentiating synthetic compound ("9"); the screening method for a substance for inhibiting or promoting a response to an immunopotentiating synthetic compound according to any one of "7" to "9", wherein the substance for inhibiting or promoting a response to an immunopotentiating synthetic compound is an substance for inhibiting or promoting against a viral infectious disease ("10"); the screening method for a substance for inhibiting or promoting a response to an immunopotentiating synthetic compound according to any one of "7" to "9", wherein the substance for inhibiting or promoting a response to an immunopotentiating synthetic compound is an agonist or an antagonist to TLR7 ("11"); the screening method for a substance for inhibiting or promoting a response to an immunopotentiating synthetic compound according to any one of "7" to "11", wherein the immunopotentiating synthetic compound is an imidazoquinoline group compound ("12"); and the screening method for a substance for inhibiting or promoting a response to an immunopotentiating synthetic compound according to "12", wherein the imidazoquinoline group compound is R-848 ("13").

The present invention further relates to a substance for inhibiting or promoting a response to an immunopotentiating synthetic compound, obtained from the screening method for substances for inhibiting or promoting a response to an immunopotentiating synthetic compound according to any one of "7" to "13" ("14"); the substance for inhibiting or promoting a response to an immunopotentiating synthetic compound according to claim 14, wherein the substance for inhibiting or promoting a response to an immunopotentiating synthetic compound is a substance for inhibiting or promoting against a viral infectious disease ("15"); the substance for inhibiting or promoting a response to an immunopotentiating synthetic compound according to "14", wherein the substance for inhibiting or promoting a response to an immunopotentiating synthetic compound is an agonist or an antagonist to TLR7 ("16").

The present invention still further relates to a screening method for an immunopotentiating synthetic compound, wherein an immunopotentiating effect in immune cells derived from the non-human animal model unresponsive to an immunopotentiating synthetic compound according to any one of "1" to "6" is measured/evaluated with the use of the aforementioned immune cells derived from the non-human animal model and a test synthetic compound ("17"); a screening method for an immunopotentiating synthetic compound, wherein the immunopotentiating effect in the non-human animal model unresponsive to an immunopotentiating synthetic compound according to any one of "1" to "6", is measured/evaluated with the use of the aforementioned non-human animal model and a test synthetic compound ("18"); a screening method for an immunopotentiating synthetic compound, wherein the immunopotentiating effect in immune cells derived from the non-human animal model unresponsive to an immunopotentiating synthetic compound according to any one of "1" to "6", and in immune cells derived from the wild-type non-human animal are measured/compared and evaluated with the use of immune cells derived from the aforementioned non-human animal model, immune cells derived from the wild-type non-human animal model as a control, and a test synthetic compound ("19"); a screening method for an immunopotentiating synthetic compound, wherein the immunopotentiating effect in the non-human animal model unresponsive to an immunopotentiating synthetic compound according to any one of "1" to "6" and in the wild-type non-human animal are measured/compared and evaluated with the use of the aforementioned non-human animal model, the wild-type non-human animal model as a control, and a test synthetic compound ("20"); the screening method for the immunopotentiating synthetic compound according to any one of "17" to "20", wherein imiquimod or R-848 is a lead compound ("21"); and an immunopotentiating synthetic compound obtained from the screening method according to "21", wherein imiquimod or R-848 is used as a lead compound ("22").

BEST MODE FOR CARRYING OUT THE INVENTION

Figure 1:
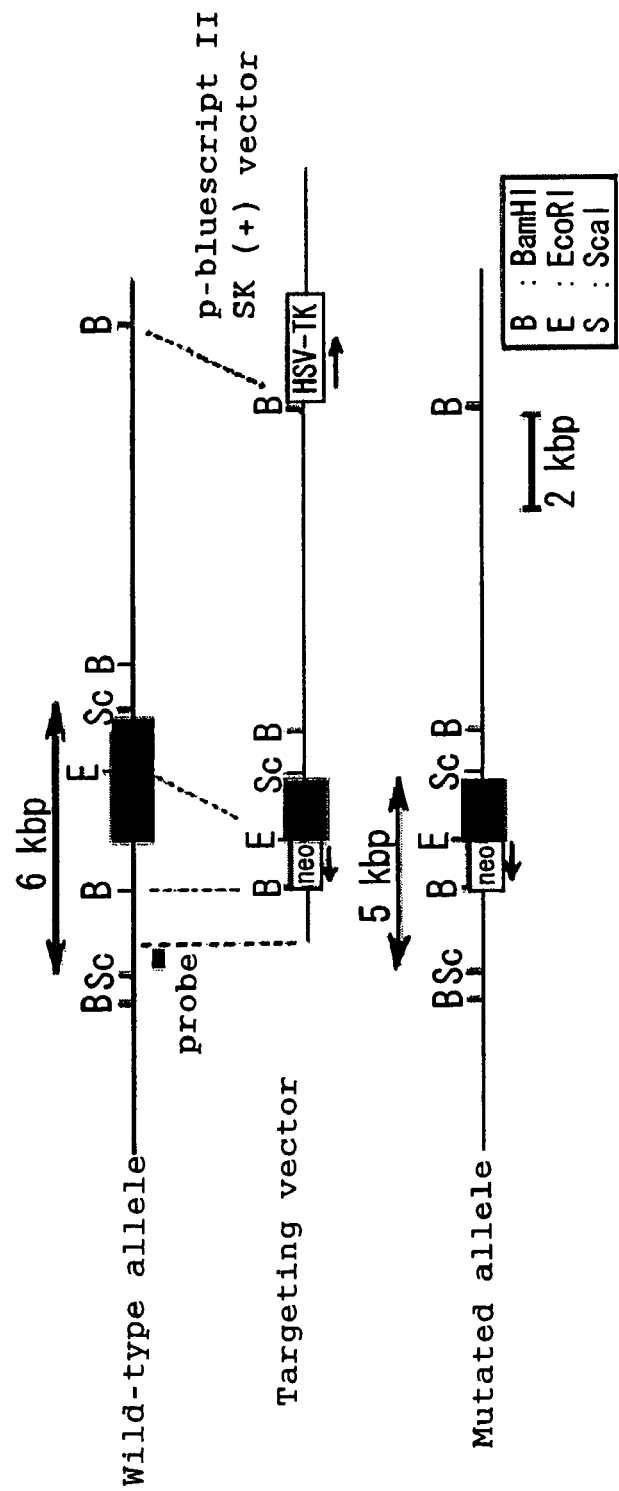
FIG. 1 is a figure that shows gene maps indicating mouse TLR7 gene locus, targeting vector and mutated allele by mutation.

As for the non-human animal model unresponsive to an immunopotentiating synthetic compound of the present invention, it is not particularly limited as long as it is a non-human animal wherein a gene function encoding TLR7 that recognizes an immunopotentiating synthetic compound lacks on its genomic locus. As for an immunopotentiating synthetic compound, any synthetic compound can be exemplified as long as it is an immunopotentiating synthetic compound which can be recognized by TLR7, for example, an imidazoquinoline group compound, more specifically the above-mentioned imiquimod, R-848 and the like can be exemplified.

Therefore, the non-human animal model unresponsive to a synthetic compound of the present invention relates to a non-human animal wherein the reactivity to stimulation by immunopotentiating synthetic compound of the living body, or the reactivity of the cells, tissues or organs constituting the living body is specifically decreased or deleted compared to wild-type non-human animal, for example an animal other than human such as mice, rats, rabbits and the like that has reactivity to stimulation by bacteria DNA having unmethylated CpG sequence, while the reactivity of the living body or the reactivity of the cells, tissues or organs constituting the living body to an immunopotentiating synthetic compound such as an imidazoquinoline group compound is decreased or deleted, and a non-human animal which lacks TLR7 gene function on its chromosone such as TLR7 knockout mouse, can be specifically exemplified. Moreover, as for the aforementioned stimulation by an immunopotentiating synthetic compound, stimulation in vivo where an immunopotentiating synthetic compound is administered to a living body, stimulation in vitro wherein cells separated from a living body is contacted with an immunopotentiating synthetic compound and the like can be exemplified.

Next, the generating method for a non-human animal model unresponsive to an immunopotentiating synthetic compound of the present invention will be explained, taking a TLR7 knockout mouse as an example. With a gene fragment obtained from a mouse gene library by PCR method or the like, a gene encoding TLR7 is screened, and the screened gene which encodes TLR7 is subcloned with the use of a viral vector or the like and identified by DNA sequencing. A targeting vector is constructed by replacing whole or part of this gene encoding TLR7 with a pMC1neo gene cassette or the like, and introducing a gene such as a diphtheria toxin A fragment (DT-A) gene or a herpes simplex virus thymidine kinase gene (HSV-tK) into 3'-terminal side.

This constructed targeting vector is linearized and introduced into ES cells by a method such as electroporation for homologous recombination, and then selecting the ES cells which are homologously recombined by an antibiotic such as G418 or ganciclovir (GANC) among those recombinants. It is preferable to confirm by Southern blotting analysis etc. whether this selected ES cells are the targeted recombinants. The clone of the confirmed ES cell is microinjected into blastocyst of mouse, and the blastocyst is transplanted into a uterus of a recipient mouse to generate a chimeric mouse. A heterozygout mouse (F1 mouse: +/−) can be obtained by intercrossing this chimeric mouse with a wild-type mouse, and a TLR7 knockout mouse of the present invention can be generated by intercrossing these heterozygote mice. In addition, as a confirming method for whether TLR7 is produced in a TLR7 knockout mouse, a examining method by Northern blotting or the like by isolating RNA from the mouse obtained by the above-mentioned method, or a examining method for the expression of TLR7 in this mouse by Western blotting or the like can be exemplified.

Moreover, it can be confirmed that generated TLR7 knockout mouse was unresponsive to an immunopotentiating synthetic compound, for example by contacting an immunopotentiating synthetic compound with immune cells such as macrophages, mononuclear cells, or dendritic cells of TLR7 knockout mouse in vitro or in vivo, to measure the production level of TNF-α, IL-6, IL-12, IFN-γ and the like in the cells, the proliferative response of splenic B cells, expression level of antigens such as CD40, CD80, CD86, and MHC class II on the surface of splenic B cells, and activation of a molecule in signal transduction pathway of TLR7 such as NF-κB, JNK, and IRAK. Thus, the TLR7 knockout mouse of the present invention can be a useful model on elucidating action mechanism of an immunopotentiating synthetic compound, and devising a treatment strategy for viral infection.

Meanwhile, homozygotic non-human animals born at the expected Mendelian ratios include TLR7-deficient types recognizing an immunopotentiating synthetic compound and the wild-types of their littermates. Precise comparative experiments can be conducted at an individual level by using the deficient types and their littermates of wild-types in therefore it is preferable to combine a wild-type non-human animal, preferably a wild-type non-human animal as the same species as the non-human animal whose gene function encoding TLR7 recognizing an immunopotentiating synthetic compound is deficient on its genomic locus and its littermate, for example in screening substances for inhibiting or promoting a response to an immunopotentiating synthetic compound of the present invention, as described below.

The non-human animal model unresponsive to an immunopotentiating synthetic compound of the present invention, and immune cells such as macrophages, splenic cells and dendritic cells derived from the non-human animal model, can be used for screening various kinds of viral infectious diseases by various kinds of viral infection such as herpesvirus, cytomegalovirus, and human papillomavirus, or for screening substances for inhibiting or promoting a response to an immunopotentiating synthetic compound such as an agonist or an antagonist to TLR7, besides for elucidating action mechanism of an immunopotentiating synthetic compound. The screening method for substances for inhibiting or promoting a response to viral infectious diseases such as pudendal wart, or substances for inhibiting or promoting a response to an immunopotentiating synthetic compound such as an agonist or an antagonist to TLR7 will be described with examples in the following.

As for a screening method for substances for inhibiting or promoting a response to the immunopotentiating synthetic compound of the present invention, a method for measuring/evaluating the response to an immunopotentiating synthetic compound in the immune cells such as macrophages, splenic cells, and dendritic cells derived from the non-human animal model unresponsive to an immunopotentiating synthetic compound, with the use of the immune cells, a test substance, and an immunopotentiating synthetic compound, or a measuring/evaluating method for the response to an immunopotentiating synthetic compound in the non-human animal model with the use of the non-human animal model unresponsive to an immunopotentiating synthetic compound, a test substance, and an immunopotentiating synthetic compound, can be exemplified.

As for the aforementioned screening method by using immune cells derived from non-human animal model unresponsive to an immunopotentiating synthetic compound, a method of contacting immune cells obtained from the non-human animal model unresponsive to an immunopotentiating synthetic compound with a test substance beforehand in vitro, then culturing the immune cells in the presence of an immunopotentiating synthetic compound, and measuring/evaluating the response to an immunopotentiating synthetic compound in the immune cells, and a method of contacting immune cells obtained from the non-human animal model unresponsive to immunopotentiating synthetic compound with an immunopotentiating synthetic compound beforehand in vitro, then culturing the immune cells in the presence of the test substance, and measuring/evaluating the response to an immunopotentiating synthetic compound in the immune cells, can be exemplified.

Further, a method of administering the test substance to the non-human animal model unresponsive to an immunopotentiating synthetic compound beforehand, and then culturing the immune cells obtained from the non-human animal in the presence of an immunopotentiating synthetic compound, and measuring/evaluating the response to the immunopotentiating synthetic compound in the immune cells, and a method of administering the test substance to the non-human animal model unresponsive to an immunopotentiating compound of the present invention beforehand, then administering the immunopotentiating synthetic compound to the non-human animal, and measuring/evaluating the response to an immunopotentiating synthetic compound in the immune cells obtained from the non-human animal can be exemplified.

In addition, a method of administering the immunopotentiating synthetic compound to the non-human animal model unresponsive to an immunopotentiating synthetic compound of the present invention beforehand, then culturing the immune cells obtained from the non-human animal in the presence of the test substance, and measuring/evaluating the response to the immunopotentiating synthetic compound in the immune cells, and a method of administering the immunopotentiating synthetic compound to the non-human animal model unresponsive to an immunopotentiating synthetic compound of the present invention beforehand, then administering the test substance to the non-human animal, and measuring/evaluating the response to the immunopotentiating synthetic compound in the immune cells obtained from the non-human animal, can be exemplified.

On the other hand, as for a measuring/evaluating method for the response to the immunopotentiating synthetic compound in the non-human animal model using the non-human animal model unresponsive to an immunopotentiating synthetic compound of the present invention, the test substance, and the immunopotentiating synthetic compound, a method of administering the test substance to the non-human animal model unresponsive to an immunopotentiating synthetic compound beforehand, then administering the immunopotentiating synthetic compound to the non-human animal model, and measuring/evaluating the response to an immunopotentiating synthetic compound in the non-human animal model, and a method for infecting the non-human animal model unresponsive to an immunopotentiating synthetic compound with the immunopotentiating synthetic compound beforehand, then administering the test substance to the non-human animal model, and measuring/evaluating the response to the immunopotentiating synthetic compound in the non-human animal model, can be exemplified.

The measurement/evaluation of the response to the immunopotentiating synthetic compound in the present invention relates to a measurement/evaluation of the function of a specific response to the immunopotentiating synthetic compound, and signal transduction into the cells. As for a function of signal transduction, a function for producing cytokine such as TNF-α, IL-6, IL-12 and IFN-γ, a function of generating nitrite ion, a function of proliferating cells, a function of expressing antigen such as CD40, CD80, CD86 and MHC class II on the cell surface, a function of activating molecule in the signal transduction pathway of TLR7 such as NF-κB, JNK and IRAK, and the like can be specifically exemplified but it is not limited to these. Moreover, as mentioned above, in measuring/evaluating the response to the immunopotentiating synthetic compound, it is preferable to measure/evaluate with the measured value of a non-human animal model, especially that of a non-human animal model of its littermate as a control, because dispersion by individual difference can be reduced.

By using the non-human animal model unresponsive to an immunopotentiating synthetic compound of the present invention, or the immune cells derived from the non-human animal model, it is possible to screen the immunopotentiating synthetic compound. In other words, as for a screening method the immunopotentiating synthetic compound of the present invention, it is not particularly limited as long as it is a method for measuring/evaluating the immunopotentiating effect in the immune cells derived from the above-mentioned non-human animal model, using the immune cells derived from the non-human animal model unresponsive to an immunopotentiating synthetic compound of the present invention and a test synthetic compound, or a method for measuring/evaluating the immunopotentiating effect in the above-mentioned non-human animal model, using the non-human animal model unresponsive to an immunopotentiating synthetic compound of the present invention and the test synthetic compound.

As for a screening method by using the above-mentioned immune cells derived from the non-human animal model, a method of contacting immune cells such as macrophages, splenic cells and dendritic cells obtained from the non-human animal model, with the test synthetic compound in vitro, and then measuring/evaluating immunopotentiating effect in the immune cells, and a method of administering the test synthetic compound to the non-human animal model, and then measuring/evaluating immunopotentiating effect in the immune cells obtained from the non-human animal model, can be exemplified.

As for a screening method by using the above-mentioned non-human animal model, a method of administering the test synthetic compound to the non-human animal model, and then measuring/evaluating immunopotentiating effect the animal model can be exemplified.

The measurement/evaluation of immunopotentiating effect in the screening method for the immunopotentiating synthetic compound of the present invention relates to measurement/evaluation of the level of function, for example, a function for producing cytokine such as IFN-α, TNF-α, IL-6, IL-12 and IFN-γ, a function of producing nitrite oxide, a function of proliferating cells, a function of expressing antigen such as CD40, CD80, CD86 and MHC class II on the cell surface, and a function for activating molecules in signaling pathway of TLR7 such as NF-κB, JNK and IRAK, in the immune cells derived from the non-human animal model unresponsive to an immunopotentiating synthetic compound. For instance, by using the method of combinatorial chemistry or the like, using imiquimod or R-848 as a lead compound, when the screening of the above-mentioned immunopotentiating synthetic compound is performed and the behavior in the non-human animal model or in the immune cells derived from the non-human animal model is similar to that in using the lead compound, the test synthetic compound has a high possibility to be a candidate substance of the immunopotentiating synthetic compound. Further, the immunopotentiating synthetic compound obtained from the method for screening by using imiquimod or R-848 as a lead compound is included in the present invention.

Further, by using the non-human animal model unresponsive to an immunopotentiating synthetic compounds of the present invention and the immune cells derived from the non-human animal model, and a wild-type non-human animal and the immune cells derived from the wild-type non-human animal as control, it is possible to screen the immunopotentiating synthetic compound. In other words, as for a screening method the immunopotentiating synthetic compound unresponsive to an immunopotentiating synthetic compound of the present invention, it is not particularly limited as long as it is a method for measuring/comparing the immunopotentiating effect the non-human animal model unresponsive to an immunopotentiating synthetic compound of the present invention and that from a wild-type non-human animal with the use of the immune cells derived from the non-human animal model unresponsive to an immunopotentiating synthetic compound of the present invention, the immune cells derived from the wild-type non-human animal model as a control and the test synthetic compound, or a method for measuring/comparing and evaluating the immunopotentiating effect in the non-human animal model and the wild-type non-human animal model with the use of the non-human animal model, the wild-type non-human animal as a control and the test synthetic compound.

As for a screening method by using the aforementioned immune cells derived from the non-human animal model and those from the wild-type non-human animal as a control, a method of contacting the immune cells such as macrophages, splenic cells and dendritic cells obtained from the non-human animal model and the wild-type non-human animal with the test synthetic compound in vitro, respectively, and then measuring/comparing and evaluating the immunopotentiating effect in the immune cells, and a method for administering the test synthetic compound to the non-human animal model and the wild-type non-human animal, and then measuring/comparing and evaluating the immunopotentiating effect in the immune cells obtained from the non-human animal model respectively and the wild-type non-human animal, can be exemplified.

As for a screening method by using the above-mentioned non-human animal model and the wild-type non-human animal as a control, a method of administering the test synthetic compound to the non-human animal model and the wild-type non-human animal respectively, and then measuring/comparing and evaluating the immunopotentiating effect in the non-human animal model and the wild-type non-human animal, can be exemplified.

The measuring/comparing and evaluating of immunopotentiating effect in the screening method for immunopotentiating synthetic compound of the present invention relates to measure the level of for example, a function for producing cytokine such as IFN-α, TNF-α, IL-6, IL-12 and IFN-γ, a function for producing nitrite ion, a function for proliferating cells, a function of expressing antigen such as CD40, CD80, CD86 and MHC class II on the cell surface, and a function for activating molecules in signaling pathway of TLR7 such as NF-κB, JNK and IRAK, in the non-human animal model unresponsive to immunopotentiating synthetic compound or the immune cells derived from the non-human model animal and the wild-type non-human animal model or the immune cells derived from the wild-type non-human animal model as a control, respectively and to compare/evaluate the level of the function. For instance, the test synthetic compound which induces the generation of cytokine in the wild-type non-human animal, while it does not induce the generation of cytokine in the non-human animal model, has a high possibility to be a candidate substance for the immunopotentiating synthetic compound. Further, by using the method of combinatorial chemistry or the like, using imiquimod or R-848 as a lead compound, when the screening of the aforementioned immunopotentiating synthetic compound results in the similarity between the behavior in the non-human animal model or the immune cells derived from the non-human animal model, and that in the immune cells derived from the wild-type non-human animal or the non-human animal model as a control, the test synthetic compound has a high possibility to be a candidate substance for the immunopotentiating synthetic compound. Further, the immunopotentiating synthetic compound obtained from the / screening method with imiquimod or R-848 as a lead compound is included in the present invention.

As it was revealed that TLR7 is involved in the recognition of the immunopotentiating synthetic compound, by the non-human animal model that lacks reactivity specifically to the immunopotentiating synthetic compound of the present invention, it is thought that the non-human animal model will become an extremely useful animal model in devising a treatment strategy for various kinds of viral infectious diseases by various kinds of viral infections such as herpesvirus, cytomegalovirus, and human papillomavirus, as well as in elucidating the action mechanism of the immunopotentiating synthetic compound. Moreover, there is a possibility for an agonist and an antagonist of TLR7 to be substances for inhibiting or promoting the aforementioned various kinds of viral infectious diseases, and useful substances for diagnose/treatment for diseases and the like caused by deletion or abnormality of TLR7 activity.

The present invention will be explained more specifically with examples and reference example in the following, but the technical scope of the invention is not limited to these examples and the like.

The followings were used as reagents and the like in the examples.

DNA derived from *Escherichia coli* and DNA derived from *Micrococcus deikticus* were purchased from Sigma, and further purified with phenol/chloroform extract. LPS derived from *Salmonella minnesota* Re-595 was purchased from Sigma. Mycoplasma polypeptide MALP-2 used was provided by Dr. Peter F. Muhlradt (Institute of Immunology, Philipps University, Germany) was used. All of the used ODNs (oligodeoxynucleotide) were purchased from Hokkaido System Science Co., Ltd. In addition, the sequence and backbone of CpGDNA are as follows:

Phosphorothioate 1688: tccatgacgttcctgatgct (Seq. ID No. 1)

D19: ggTGCATCGATGCAgggggg (Seq. ID No. 2)

ACC-30: ACCGATAACGTTGCCGGTGACGGCACCACG (Seq. ID No. 3)

Phosphodiester 1688: TTCATGACGTTCCTGATGCT (Seq. ID No. 4)

The underlined portions show typical CpG motifs. Capital and lower-case letters indicate the phosphodiester backbone (natural backbone) and phosphothioate modification, respectively.

REFERENCE EXAMPLE 1

Generation of MyD 88 Knockout Mice

MyD88 gene was screened from 129/SvJ mouse gene library (Stratagene), subcloned in pBluescript vector (Stratagene), and identified by restriction mapping and DNA sequencing. Targeting vector was constructed by replacing 1.0-kb gene fragment with a neomycine resistant gene from pMC1neo (Stratagene). The replaced gene fragment included two exons encoding domain similar to the cytoplasmic domain of IL-1RacP (receptor accessory protein). The neomycine resistant gene comprised a 1.1-kb 5' gene fragment of and a 5.2-kb 3' gene fragment as flanking sequences. Next, HSV-tk cassette was introduced to 3' terminal of the gene fragment. ES cell E 14.1 was transfected with linearized marker vector, and selected with G418 and gansiclovir. The targeted ES clone comprising mutated MyD88 alleles was microinjected into the blastocyst of C57BL/6 mice. The obtained chimeric mice were crossed with C57BL/6 female mice in order to generate heterozygote mice. The heterozygote mice were intercrossed to obtain homozygotic mice, and thus MyD88 deficient mice were generated. MyD88 knockout mice grew healthy, not showing abnormality by the age of 20 weeks.

REFERENCE EXAMPLE 2

Generation of TLR9 Knockout Mice

TLR9 genome DNA was isolated from 129/SvJ mouse gene library (Stratagene) with a probe derived from mouse TLR9 gene (reg. AF245704), subcloned in pBluescript II SK (+) vector (Stratagene), and identified by restriction mapping and DNA sequencing. Targeting vector was constructed by replacing 1.0-kb fragment encoding a part of LRR (leucine-rich repeat) region with a neomycine resistant gene cassette (pMC1neo; Stratagene), and inserting herpes simplex thymidine kinase (HSV-TK) as a negative selection marker. This targeting vector was linearized, electroporated into embryonic stem cells (ES cells), and the clones showing resistance to G418 and gansiclovir were selected. The targeted ES clones comprising mutated MyD88 alleles were microinjected into the blastocysts of C57BL/6 mice to generate chimeric mice. These chimeric male mice were crossed with C57BL/6 female mice to generate heterozygote F1 mice, and homozygotic mice (TLR9 knockout mice: TLR9 $^{-/-}$) were obtained by intercrossing the heterozygote F1 mice. TLR9 knockout mice grew healthy, not showing abnormality by the age of 20 weeks.

EXAMPLE 1

Generation of TLR7 Knockout Mice

TLR7 genome DNA was screened with a probe (Seq. ID No. 5) derived from human genome DNA sequence (reg. AC003046) comprising a human TLR7 gene from 129/SvJ mouse gene library (Stratagene), subcloned in pBluescript II SK (+) vector (Stratagene), and identified by restriction mapping and DNA sequencing. Targeting vector was constructed by replacing 1.8-kb TLR7 gene fragment encoding a part of leucine-rich repeat with a neomycine resistant gene cassette (pMC1-neo; Stratagene), and inserting herpes simplex thymidine kinase (HSV-TK) as a negative selection marker. The gene loci of mouse TLR7, the targeting vector, and mutated allele by mutation are shown in FIG. 1. In FIG. 1, "■" shows coding exons. The restriction enzymes used were ScaI (Sc) and BamHI (B). This targeting vector was linearized, electroporated into E 14.1 embryonic stem (ES) cells, 340 clones showing resistance to G418 and gansiclovir were selected, and six clones were screened by PCR method and Southern blotting.

Figure 2:
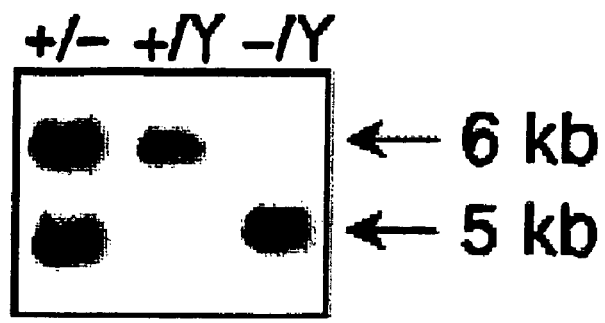
FIG. 2 is a photograph that shows the result of Southern blotting analysis of TLR7 knockout mouse of the present invention.

Three targeted ES clones comprising mutated TLR7 alleles were microinjected into the blastocyst of C57BL/6 mice to generate chimeric mice wherein the mutated alleles were transduced through the germ cell line. These male chimeric mice were crossed with C57BL/6 female mice to generate female mice, all of the obtained female mice were heterozygote mice. This was because TLR7 was mapped to X genomic locus, and all of the germ cell lines were transducted. In order to generate TLR7 knockout mice, homozygotic mice (TLR7 knockout mice: TLR7 $^{-/-}$) were obtained by intercrossing the obtained heterozygote female mice with heterozygote mice (F1). In the meantime, ascertainment of homozygotic mice was conducted by digesting each genomic DNA extracted from murine tail with ScaI and by Southern shown in FIG. 2, a 6-kb single band, a 5-kb band (−/Y), and both bands were shown in wild-type male mice (+/Y), hemizygous male mice, and hemizygous female mice, respectively. The TLR7 knockout mice of the present invention (TLR7 $^{-/-}$) could be generated according to Mendelian rate, not showing significant abnormality by 25th week.

EXAMPLE 2

Figure 3:
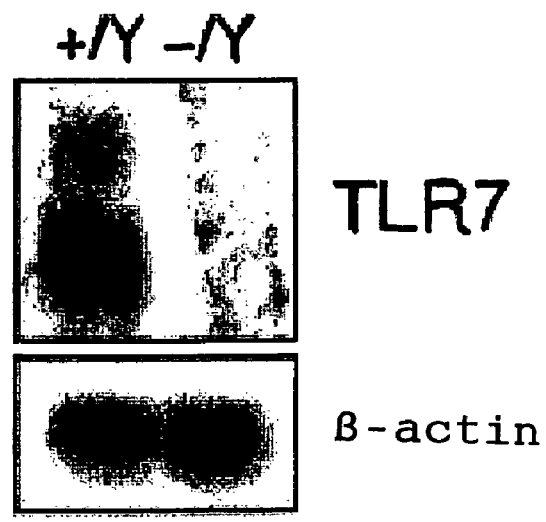
FIG. 3 are photographs that show the result by Northern blotting analysis of TLR7 knockout mouse of the present invention.

Preparation of Peritoneal Macrophage 2 ml of 4% thioglycollic acid medium (DIFCO) were injected into the intraperitoneals of the wild-type mice, TLR7 knockout mice (TLR7KO), MyD88 knockout mice (MyD88KO) and TLR9 knockout mice (TLR9KO), respectively, three days later, peritoneal exudate cells were isolated from intraperitoneal of each mouse, these cells were cultured in PRMI 1640 medium (GIBCO) added with 10% fatal bovine serum (GIBCO) at 37° C. for two hours, nonadherent cells were recovered by washing with Hank's buffered salt solution (HBBS; GIBCO) at iced temperature, and the adherent cells were used as peritoneal macrophages in following experiment. Total RNA (10 μg) obtained from macrophages derived from the wild-type mice (+/Y) and TLR7 knockout mouse (TLR7KO) was electrophoresed, transferred onto a nylon membrane, and hybridized with a part of TLR7 DNA, and this membrane was rehybridized with β-actin probe. It was examined by the Northern blotting. From the results shown in FIG. 3, the expression of TLR7mRNA could not be found in TLR7 knockout mice.

In addition, the measurement of cytokine generated from peritoneal macrophages was executed as follows; 7 peritoneal macrophages of $2\times10^5$ well or $5\times10^4$ well were cultured in 96-well plate respectively, and after stimulated with the above-mentioned reagents for 24 h, concentration of TNF-α, IL-12p40, IL-6 and/or IFN-α were measured by ELISA according to the manual.

EXAMPLE 3

Activating Immune Cells by Imidazoquinoline Group Compound

Figure 4:
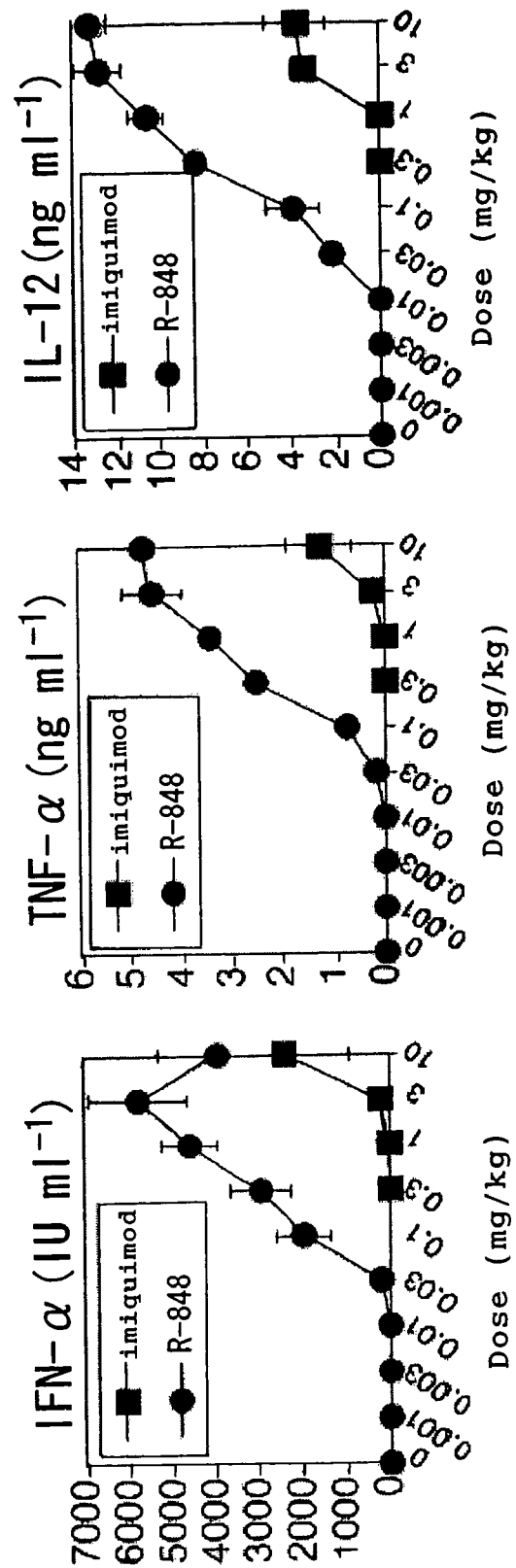
FIG. 4 is a figure that shows the result of generation of IFN-α, TNF-α and IL-12 by administrating orally imiquimod and R-848 in BALB/c mouse (wild-type).
Figure 5:
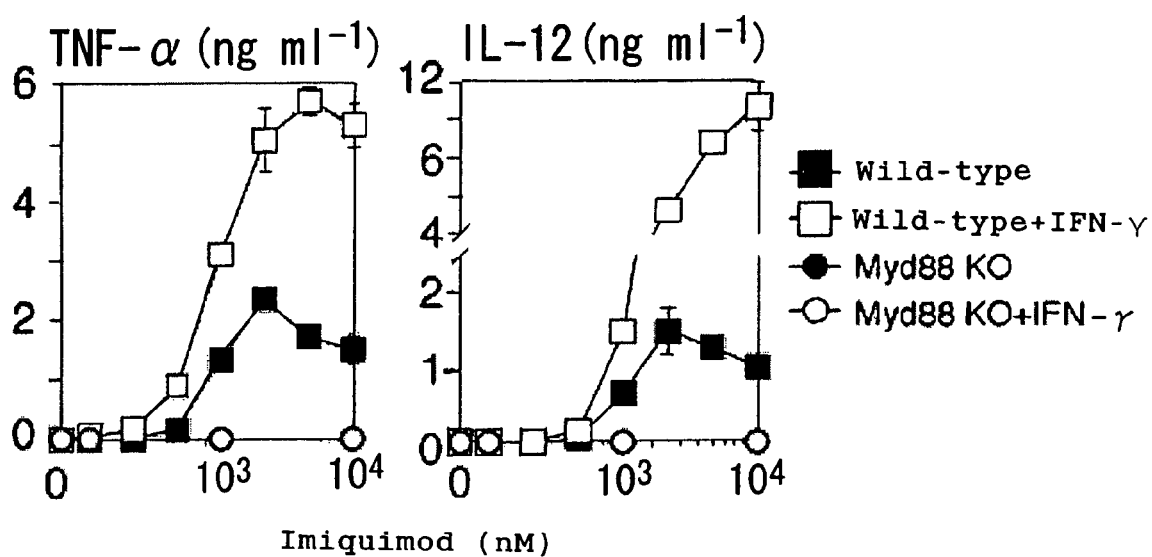
FIG. 5 is a figure that shows the result of generation of TNF-α and IL-12 by stimulation of imiquimod and R-848 in the presence or absence of IFN-γ in peritoneal macrophages derived from wild-type mice and MyD88 knockout mice.
Figure 5:
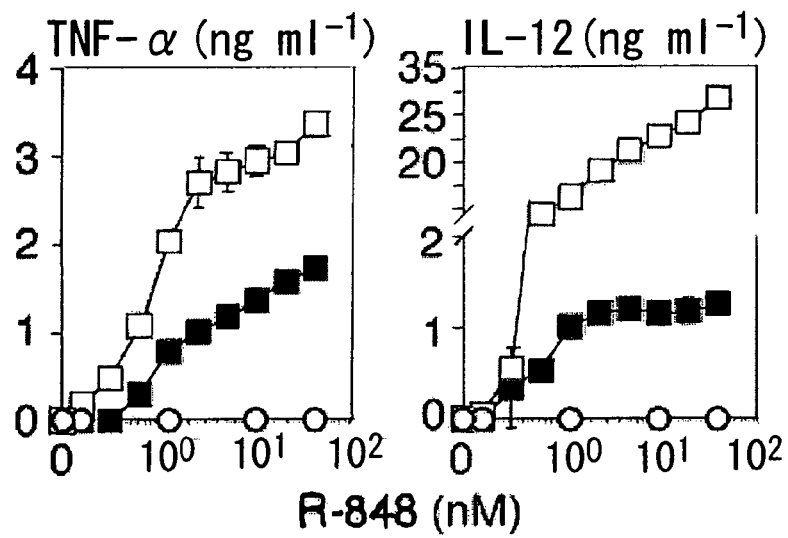

Before examining the reactivity of TLR7 knockout mice to imiquimod and R-848 which are imidazoquinoline group compound, firstly imiquimod or R-848 were administered to BALB/c mice (wild-type) orally at the predetermined concentration, respectively, the concentration of IFN-α, TNF-α and IL-12 in serum were measured after two hours. The results are shown in FIG. 4. As a result, the concentration of IFN-α, TNF-α and IL-12 in serum increased depending on applied dose. The data is shown as a mean value+/−S.D. (N=3). Similarly, the ability of these compounds to activate immune cells via TLR was examined using imiquimod or R-848 respectively. The peritoneal macrophages ($5\times10^4$ cells) from wild-type mice and MyD88 knockout mice prepared in example 2, were stimulated by imiquimod or R-848, in the presence or absence of 30 U/ml of IFN-γ, and the concentration of TNF-α and IL-12 produced by peritoneal macrophages were measured by ELISA. The results are shown in FIG. 5. As a result, the macrophages derived from wild-type mice produced cytokines such as TNF-α and IL-12 in large amount, while the macrophages derived from MyD88 knockout mice hardly produced any cytokines, which led to macrophages responding to imidazoquinoline group compounds, completely depends on MyD88. These results also revealed that imiquimod and R-848 activate immune cells via TLR. The data is shown as a mean value+/−S.D. (N=3).

EXAMPLE 4

ODN Stimulation in Macrophages Derived from TLR7KO Mice

Figure 6:
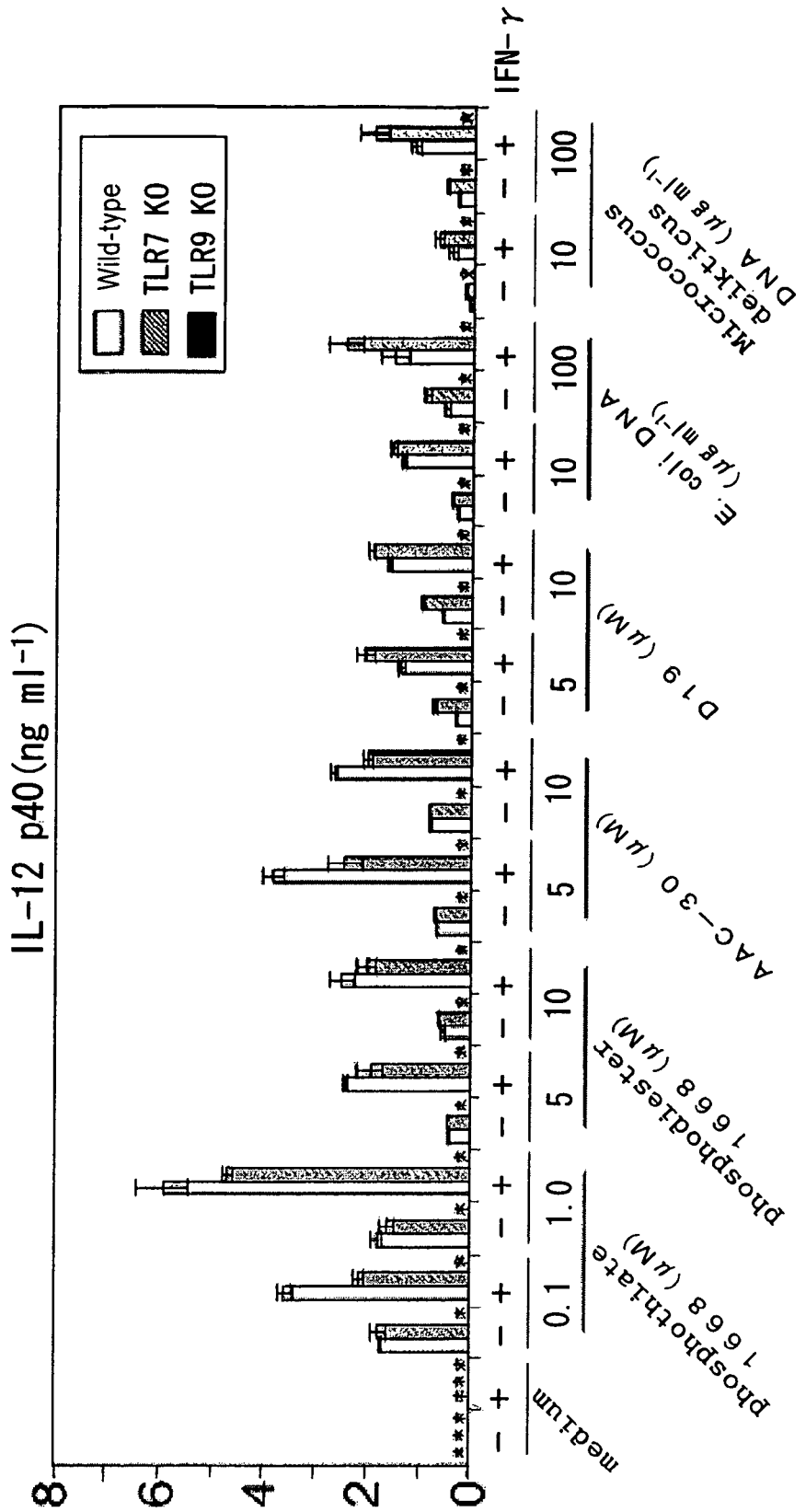
FIG. 6 is a figure that shows the result of generation of IL-12p40 by various kinds of ODN stimulation in peritoneal macrophages derived from TLR7 knockout mice and TLR9 knockout mice of the present invention.

Next, the peritoneal macrophages (5×10⁴ cells) derived from TLR7 knockout mice (TLR7KO), TLR9 knockout mice (TLR9KO) and wild-type mice were stimulated with CpGDNA 1668 (phosphorothioate 1688). D19, AAC30, natural 1688 (phosphodiester 1688). genomic DNA derived from *Escherichia coli*, or genomic DNA derived from *Micrococcus deikticus* at of a predetermined concentration in the presence (+) or absence (−) of 30 U/ml of IPN-γ, and the concentration of IL-12p40 produced by production of peritoneal macrophages contained in cultured supernatant was measured by ELISA after 24 h of culture. The results are shown in FIG. 6 (in the figure, marks of * show detection limits and below). As shown in FIG. 6, the production of IL-12p40 by various types of ODN stimulation in the peritoneal macrophages derived from TLR7 knockout mice was confirmed as in wild-type mice, while induction of production IL-12p40 was not confirmed in the peritoneal macrophages derived TLR9 knockout mice. The data is showing a mean value+/−S.D. Similar results were obtained by triplicate independent experiments.

EXAMPLE 5

Figure 7:
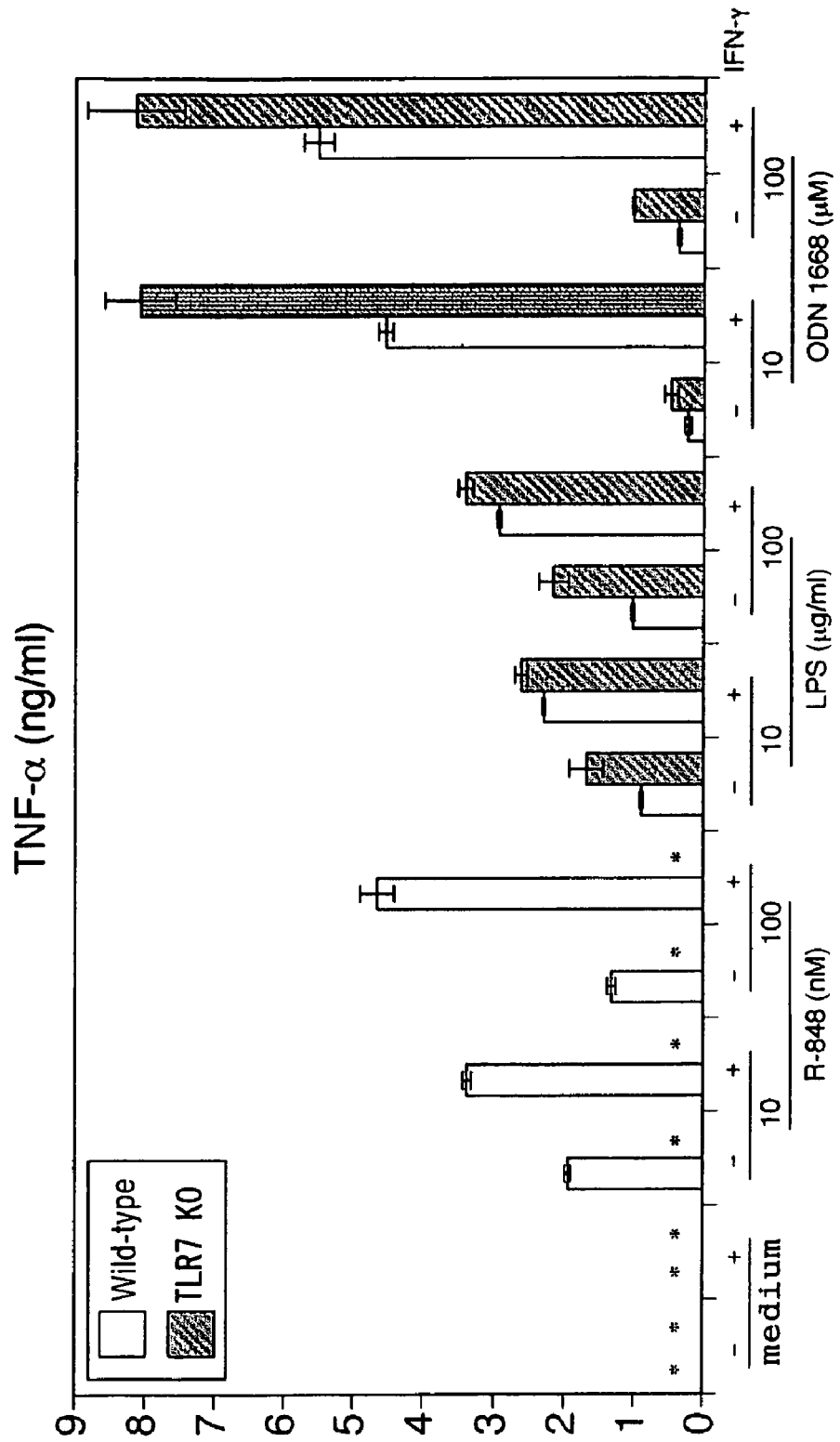
FIG. 7 is a figure that shows the result of generation of TNF-α by stimulation of chemical complex R-848, LPS, and ODN1688 in the presence or absence of IFN-γ in peritoneal macrophages derived from TLR7 knockout mice of the present invention.
Figure 8:
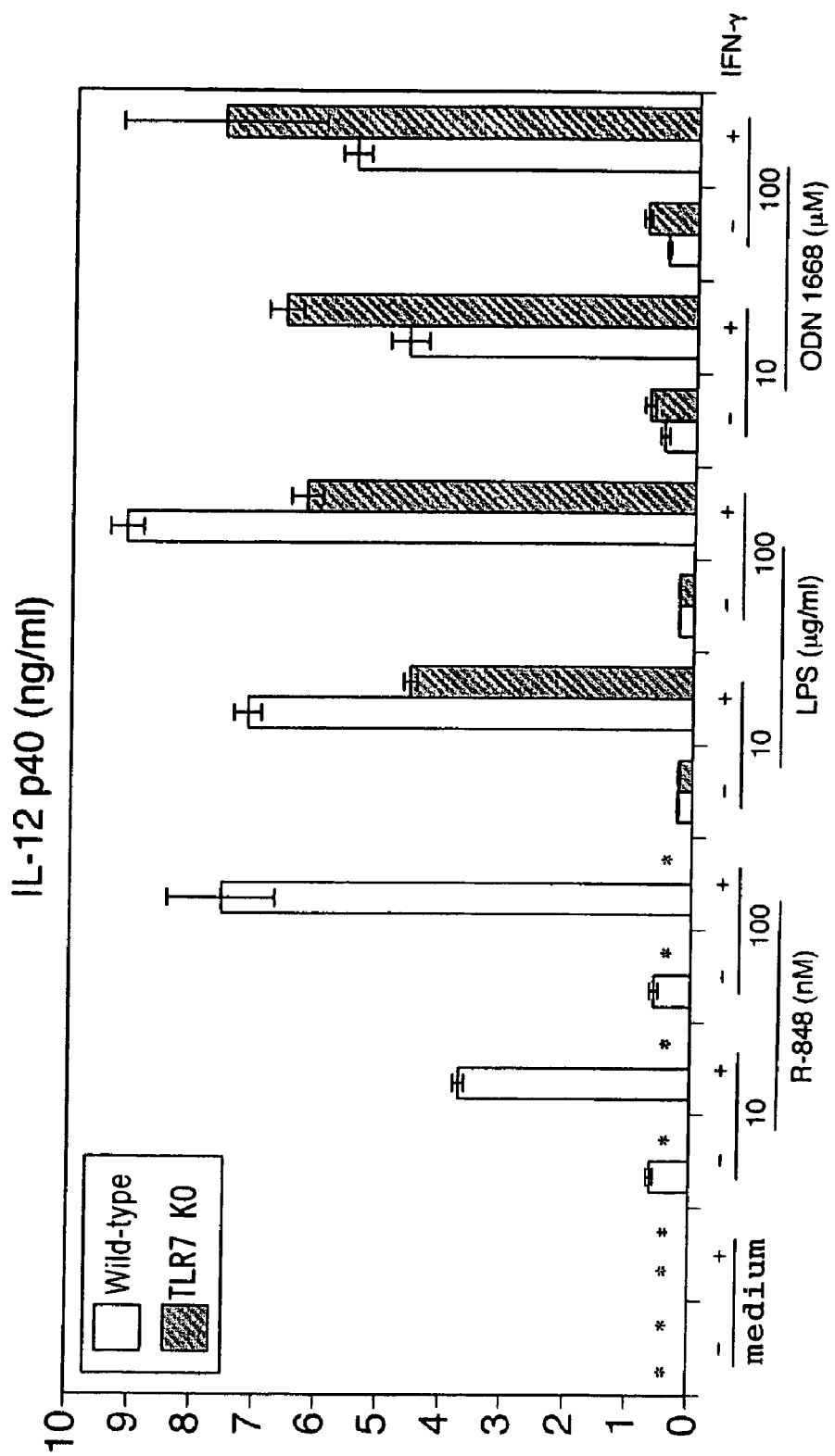
FIG. 8 is a figure that shows the result of generation of IL-12p40 by stimulation of chemical complex R-848, LPS, and ODN1688 in the presence or absence of IFN-γ in peritoneal macrophages from TLR7 knockout mice of the present invention.

Imidazoquinoline Group Compounds Stimulation in the Macrophages Derived from TLR7KO Mice Subsequently, the peritoneal macrophages (5×10⁴ cells) derived from TLR7 knockout mice (TLR7KO) and wild-type mice, were stimulated with imidazoquinoline group compound R-848, LPS and ODN 1688 (phosphorothioate 1688) at a predetermined concentration in the presence (+) or absence (−) of 30 U/ml of IFN-γ, and the concentration of TNF-α produced by peritoneal macrophages contained in cultured supernatant was measured by ELISA after 24 h of culture. The results are shown in FIG. 7 (in the figure, marks of * show detection limits and below). As shown in FIG. 7, the production of TNF-α by LPS and ODN 1688 stimulation in the peritoneal macrophages from TLR7 knockout mice was confirmed as in normal mice, while induction of production of TNF-α by imidazoquinoline group compound R-848 was not confirmed. Similarly, the concentration of IL-12p40 produced by peritoneal macrophages contained in cultured supernatant after 24 h of culture was measured by ELISA. The result are shown in FIG. 8 (in the figure, marks of * show detection limits and below). As shown in FIG. 8, the production of IL-12p40 by LPS and ODN 1688 stimulation of in the peritoneal macrophages derived from TLR7 knockout mice were confirmed as in normal mice, while induction for production of IL-12p40 by imidazoquinoline group compound R-848 was not confirmed.

EXAMPLE 6

Figure 9:
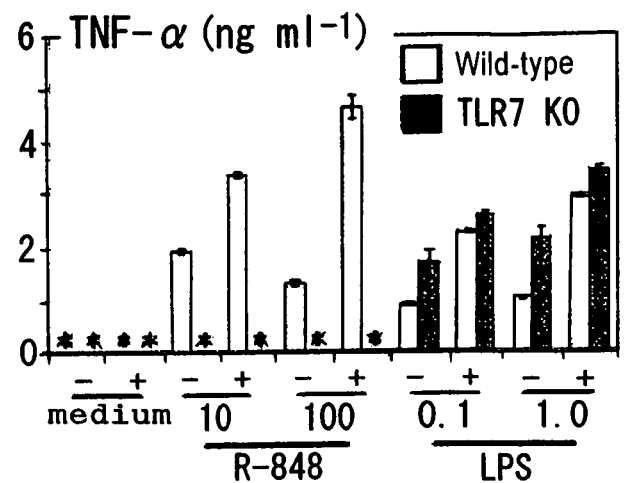
FIG. 9 is a figure that shows the result of generation of TNF-α, IL-6 and IL-12p40 by stimulation of R-848, LPS in the presence or absence of IFN-γ in peritoneal macrophages derived from TLR7 knockout mice of the present invention.
Figure 9:
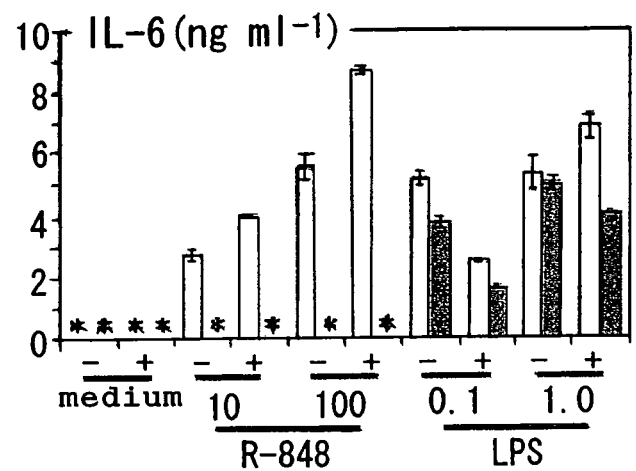
Figure 9:
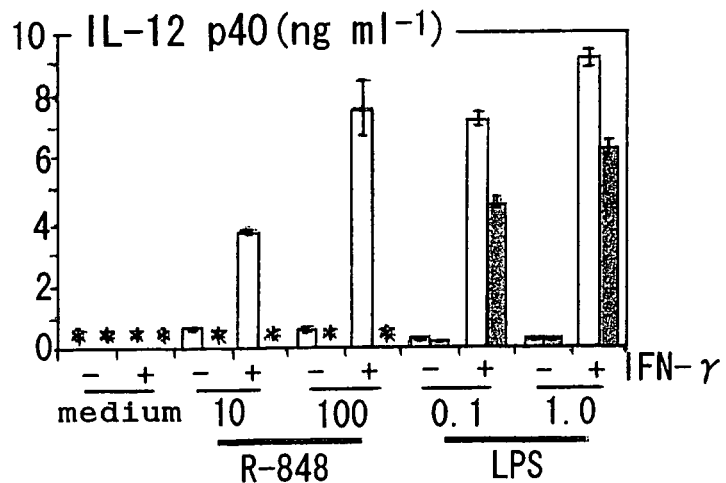

Stimulation by Imidazoquinoline Group Compounds in the Macrophages Derived from TLR7KO Mice As TLR2 knockout mice, TLR4 knockout mice, TLR6 knockout mice or TLR9 knockout mice which had already been generated by the present inventors, showed reactivity to imidazoquinoline group compounds, it was thought that TLR members except TLR2, TLR4, TLR6 and TLR9 were involved in recognizing the imidazoquinoline group compounds. Therefore, the reactivity of TLR7 knockout mice to R-848 was examined to confirm whether TLR7 recognized imidazoquinoline group compound R-848 specifically. The peritoneal macrophages (5×10⁴ cells) derived from TLR7 knockout mice (TLR7KO) and wild-type mice were stimulated with R-848 and LPS at a predetermined concentration in the presence (+) or absence (−) of 30 U/ml of IFN-γ, and the concentration of TNF-α, IL-6 and XL-12p40 produced by peritoneal macrophages contained in cultured supernatant was measured by ELISA after 24 h of culture. The results are shown in FIG. 9 (in the figure, marks of * show detection limits and below). As shown in FIG. 9, the production of TNF-α, IL-6 and IL-12p40 LPS stimulation in the peritoneal macrophages from TLR7 knockout mice was confirmed as in the wild-type mice, while induction for production of TNF-α, IL-6 and IL-12p40 was not confirmed by R-848 stimulation.

EXAMPLE 7

Figure 10:
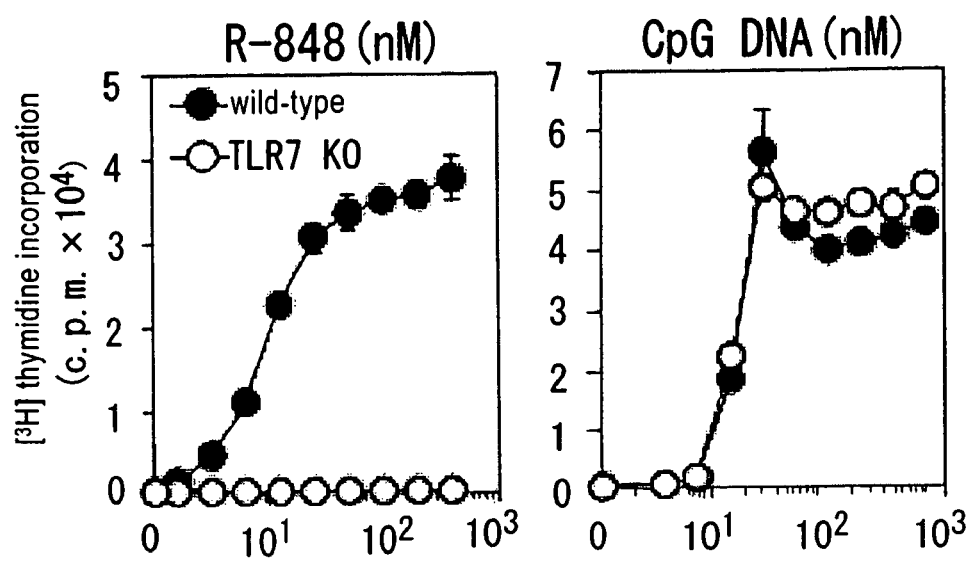
FIG. 10 is a figure that shows the result of the amount of [$^3$H] thymidine incorporation by stimulation of R-848 and CpGDNA in dendritic cells from born marrow derived from TLR7 knockout mice of the present invention.

Imidazoquinoline Group Compounds Stimulation in Splenic Cells Derived from TLR7KO Mice As activated phenotypes were proliferated and expressed by stimulating B-lymphocytes with imidazoquinoline group compounds, the proliferation of splenic cells was examined (Cell. Immunol. 203, 55-62, 2000; J. Immunol. 165, 5552-5557, 2000). Splenic cells (5×10⁴ cells) derived from TLR7 knockout mice (TLR7KO) and wild-type mice were stimulated with R-848 and CpGDNA at a predetermined concentration, cultured for 48 h (cultured by adding [³H] thymidine for last eight hours), and measured the level of thymidine incorporation using a β scintillation counter. The results are shown in FIG. 10. A mean value+/−S.D., obtained from representative experiment among triplicate experiments is shown. As shown in FIG. 10, splenic cells derived from wild-type mice showed proliferation depending on concentration, by R-848 and stimulation. On the contrary, the splenic cells derived from TLR7 knockout mice proliferated depending on concentration by CpGDNA stimulation, while they did not show proliferation by stimulation of R-848.

EXAMPLE 8

Figure 11:
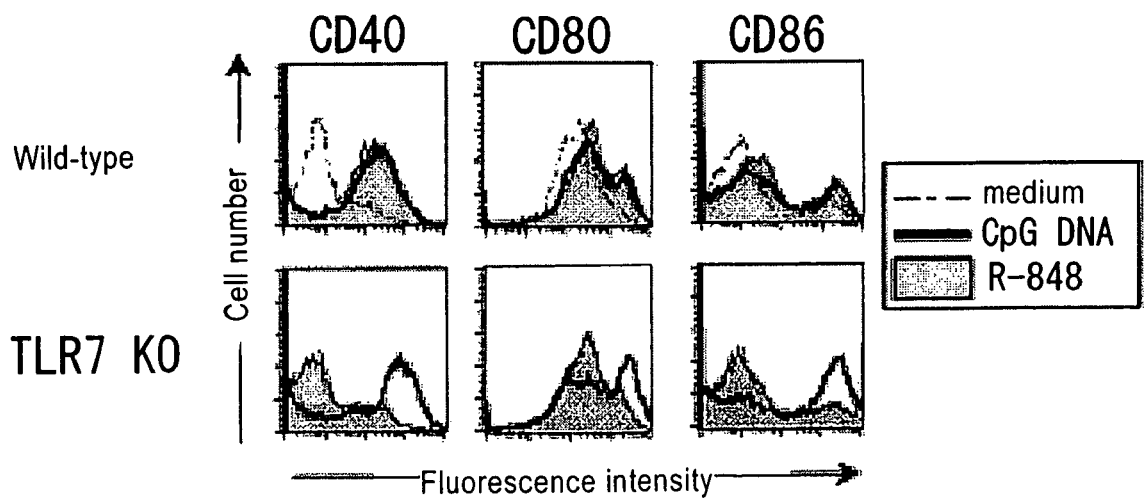
FIG. 11 is a figure that shows the result of the expression on the cell surface of CD40, CD80 and CD86 molecules by stimulation of R-848 and CpGDNA in dendritic cells from TLR7 knockout mice of the present invention.

Imidazoquinoline Group Compounds Stimulation in Dendritic Cells Derived from TLR7 KO Mice The reactivity to R-848 in dendritic cells derived from bone marrow (BMDC) derived from TLR7 knockout mice (TLR7KO) and the wild-type mice was examined. The bone marrow cells obtained from TLR7 knockout mice and wild-type mice were cultured for six days in RPMI-1640 medium supplemented with 10% fatal bovine serum and 10 ng/ml of GM-CSF (mouse granulocyte/macrophage colony stimulating factor). The obtained mouse undifferentiated dendritic cells were stimulated with R-848 or CpGDNA for 24 h, the cells were stained with biotinylated antibody to CD40, CD80 and CD86, and phycoerythrin (PE)-associated streptavidin was detected, which was analyzed by automated-cell analysing system (FACSCalibur). The results of examination of the expression of the molecules of CD40, CD80 and CD86 onto the surface of cells by flow cytometry are shown in FIG. 11. Similar to the case with CpGDNA, when BMDC derived from wild-type mice was stimulated with R-848, upregulation of CD40, CD80 and CD86 expression was induced. On the contrary, when BMDC derived from TLR7 knockout mice (TLR7KO) was stimulated with R-848, the expression of these molecules on cell surface was not enhanced.

EXAMPLE 9

Induction of NF-κB Complexes by Imidazoquinoline Group Compounds Stimulation

Figure 12:
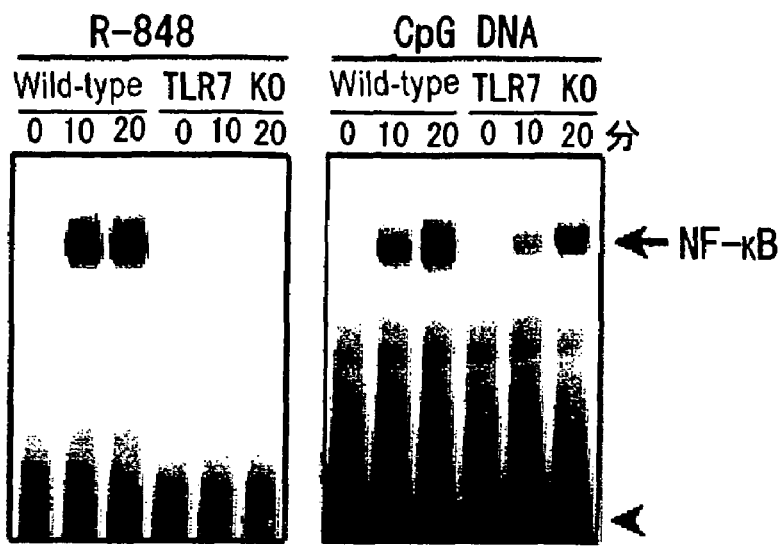
FIG. 12 are photographs that show the result of the activation of NF-κB by stimulation of R-848 and CpGDNA stimulation in macrophages derived from TLR7 knockout mice of the present invention.

Next, the activation of intracellular signaling cascade to an antiviral immune-modulator was examined. Peritoneal macrophages ($2 \times 10^6$ cells) from TLR7 knockout mice (TLR7KO) and wild-type mice respectively stimulated with thioglycollic acid, were stimulated with 100 nM of R-848 or 1.0 μM of CpGDNA 1668 (CpG) for a certain period of time, nucleoprotein was extracted, the extract obtained with the specific probe including NF-κB associated-site was incubated, electrophoresed, visualized by autoradiography, and NF-κB activation was examined as DNA-associated protein by electrophoretic mobility shift assay (EMSA). The results are shown in FIG. 12. In FIG. 12, an arrow indicates induced NF-κB complexes, and an arrow head indicates a free probe. As shown in FIG. 12, in the macrophages derived from wild-type mice, enhanced DNA avidity of NF-κB transcription, activation of c-Jun N terminal kinase (JNK), and phosphorylation of IRAK were induced when they were stimulated with imidazoquinoline group compound R-848 or CpGDNA. On the contrary, similarly to the macrophages derived from MyD88 knockout mice, all these signal event was completely destructed in macrophages derived from TLR7 knockout mice, as well.

EXAMPLE 10

Figure 13:
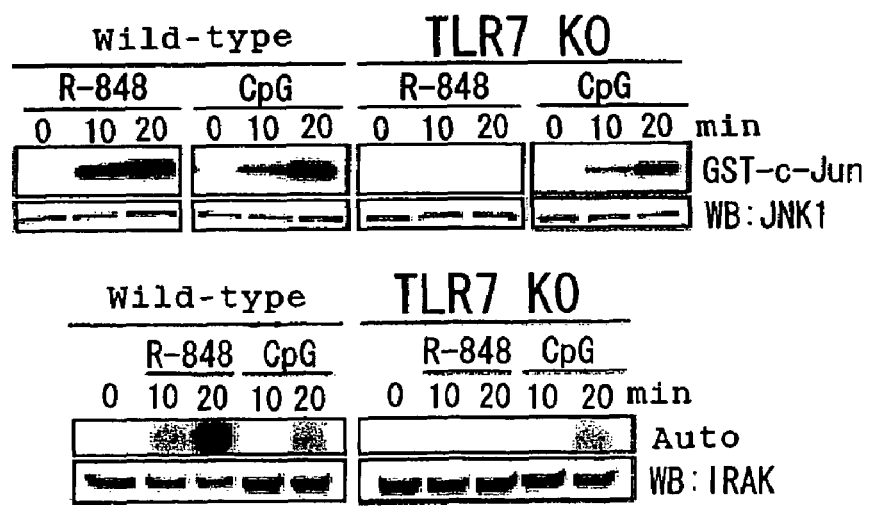
FIG. 13 are photographs that show the result of the transactivation of NF-κB reporter genes induced by R-848 in macrophages derived from TLR7 knockout mice of the present invention.

Transactivation of NF-κB Reporter Gene by Stimulation of Imidazoquinoline Group Compounds The functional role of TLR7 in transactivation of NF-κB reporter gene induced by R-848 was examined. HEK293 cells were transiently cotransfected with TLR7 expression plasmids derived from human, and luciferase activity was measured before and after R-848 stimulation. The peritoneal macrophages derived from TLR7 knockout mice (TLR7KO) and wild-type mice stimulated with thioglycollic acid were stimulated with 100 nm of R-848 or 1.0 μM of phosphothioate modified CpGDNA 1668 (CpG), all cell lysate were prepared, immunoprecipated with anti-JNK antibody, and JNK activity was examined by In Vitro Kinase Assay using GST-c-Jun fusion protein as a substrate. The results are shown in FIG. 13 (top). The same lysate was blotted with anti-JNK antibody. Moreover, the lysate was immunoprecipitated with anti-IRAK, and kinase activity of IRAK was examined by In Vitro Kinase Assay. The results are shown in FIG. 13 (bottom). The same lysate was blotted with anti-IRAK antibody. As shown in FIG. 13, NF-κB-dependent promoter to R-848 was promoted by transfection with TLR7. It is important to activate TLR7-MyD88-dependent signal pathway for the effect of imidazoquinoline in vivo.

EXAMPLE 11

Involvement of TLR7 in vivo

Figure 14:
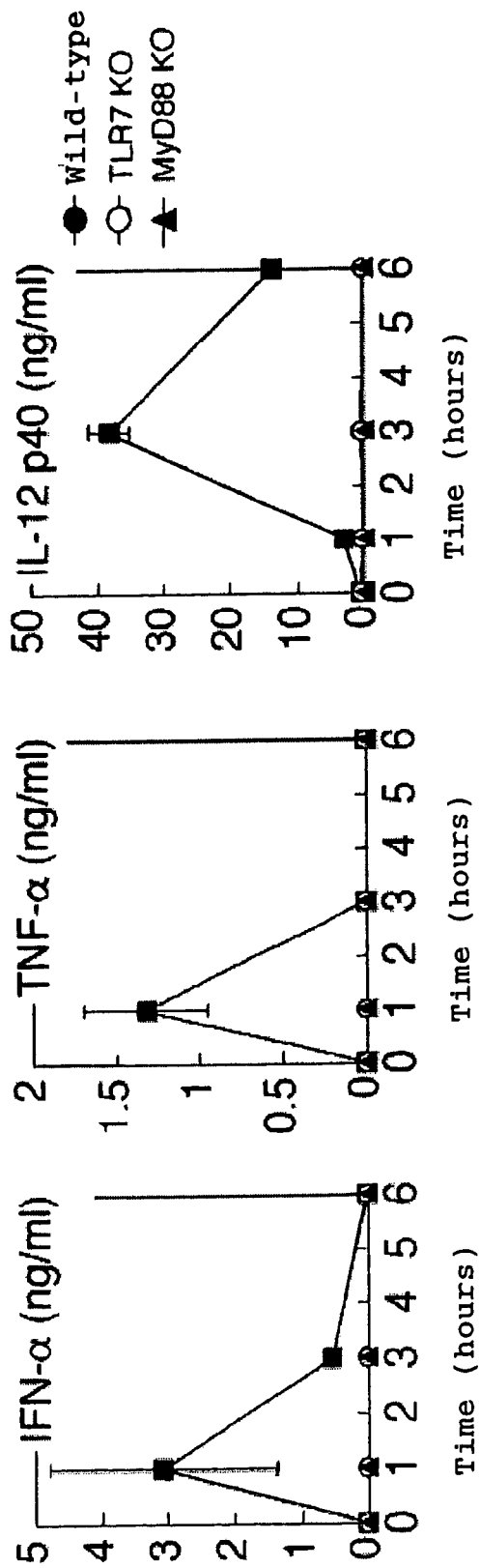
FIG. 14 is a figure that shows the result of the response in vivo to R-848 in TLR7 knockout mice of the present invention.

It was examined in vivo whether TLR7 was involved in a response to R-848. The wild-type mice, MyD88 knockout mice or TLR7 knockout mice were injected intraperitoneally with 50 nmol of R-848, the sera were harvested after a predetermined period of time, and the concentration of IFN-α, TNF-α and IL12p40 in sera was determined by ELISA. The results are shown in FIG. 14. When wild-type mice were injected with R-848 intraperitoneally, the concentration of IFN-α, TNF-α and IL12p40 in sera increased significantly. On the contrary, the increment of these cytokines was not observed in TLR7 knockout mice. Similarly, MyD88 knockout mice did not show any reactivity to R-848.

INDUSTRIAL APPLICABILITY

As the non-human animal model unresponsive to an immunopotentiating synthetic compound of the present invention is unresponsive to immunopotentiating synthetic compounds, it can not only be a very useful mouse model to elucidate action mechanism of imidazoquinoline group compounds, but also be a very useful mouse model for applying agents made by synthetic compounds such as therapeutical agents for viral infectious diseases targeting TLR7 to clinical use.

The invention claimed is:

1. A Toll-like receptor (TLR)7 homozygous knockout mouse whose genome comprises a disruption of a TLR7 gene, wherein the TLR7 homozygous knockout mouse lacks an increase of interferon-α compared with a wild-type mouse when R-848 is intraperitoneally injected into the mouse, and wherein a gene function that encodes TLR7 is deficient on its genomic locus.

2. The Toll-like receptor (TLR)7 homozygous knockout mouse according to claim 1, which is obtained by the following steps: (i) constructing a targeting vector by replacing whole or a part of a gene fragment of a gene site including an intracellular region and transmembrane region of a TLR7 gene obtained by screening a mouse gene library with a plasmid including a poly A signal and a marker gene; (ii) linearizing the targeting vector; (iii) introducing the linearized targeting vector into a mouse embryonic stem cell; (iv) microinjecting the targeted embryonic stem cell whose TLR7 gene function is deficient into a blastocyst of a mouse to generate a chimeric mouse; (v) intercrossing the chimeric mouse with a wild-type mouse to generate a heterozygote mouse; and (vi) intercrossing the heterozygote mouse.

3. The Toll-like receptor (TLR)7 homozygous knockout mouse according to claim 2, wherein the targeting vector comprises neomycin resistant gene as a marker and a diphtheria toxin A fragment (DT-A) gene or a herpes simplex virus thymidine kinase (HSV-tK) gene as a negative selection marker in 3'-terminal.

4. The Toll-like receptor (TLR)7 homozygous knockout mouse according to claim 2, wherein whole or a part of Toll-like receptor 7 gene is 1.8-kb TLR7 gene fragment encoding a part of leucine-rich repeat.

5. The Toll-like receptor (TLR)7 homozygous knockout mouse according to claim 4, wherein whole or a part of TLR7 gene is replaced with a neomycin resistant gene.

6. The Toll-like receptor (TLR)7 homozygous knockout mouse according to claim 5, wherein the neomycin resistant gene is pMC1 neo.

7. A method for producing a Toll-like receptor (TLR)7 homozygous knockout mouse whose genome comprises a disruption of a TLR7 gene, wherein the TLR7 homozygous knockout mouse lacks an increase of interferon-$\alpha$ compared with a wild-type mouse when R-848 is intraperitoneally injected into the mouse, the method comprising the following steps: (i) constructing a targeting vector by replacing whole or a part of a gene fragment of a gene site including an intracellular region and a transmembrane region of a TLR7 gene obtained by screening a mouse gene library with a plasmid including a poly A signal and a marker gene; (ii) linearizing the targeting vector; (iii) introducing the linearized targeting vector into a mouse embryonic stem cell; (iv) microinjecting the targeted embryonic stem cell whose TLR7 gene function is deficient into a blastocyst of a mouse to generate a chimeric mouse; (v) intercrossing the chimeric mouse with a wild-type mouse to generate a heterozygote mouse, and (vi) intercrossing the heterozygote mouse.

* * * * *

UNITED STATES PATENT AND TRADEMARK OFFICE
CERTIFICATE OF CORRECTION

| | | |
|---|---|---|
| PATENT NO. | : 7,608,750 B2 | Page 1 of 1 |
| APPLICATION NO. | : 10/496501 | |
| DATED | : October 27, 2009 | |
| INVENTOR(S) | : Akira et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this
Twenty-second Day of February, 2011

David J. Kappos
*Director of the United States Patent and Trademark Office*